United States Patent
Rossl et al.

(10) Patent No.: US 9,159,462 B2
(45) Date of Patent: Oct. 13, 2015

(54) DETECTION APPARATUS (75) Inventors: Ewald Rossl, Ellerau (DE); Thomas Koehler, Norderstedt (DE); Roland Proksa, Neu Wulmstorf (DE)

(73) Assignee: Koninklijke Philips N.V., Eindhoven (NL)

( * ) Notice: Subject to any disclaimer, the term of this patent is extended or adjusted under 35 U.S.C. 154(b) by 169 days.

(21) Appl. No.: 14/000,414

(22) PCT Filed: Feb. 20, 2012

(86) PCT No.: PCT/IB2012/050755
§ 371 (c)(1),
(2), (4) Date: Aug. 20, 2013

(87) PCT Pub. No.: WO2012/114250
PCT Pub. Date: Aug. 30, 2012

(65) Prior Publication Data
US 2013/0329851 A1 Dec. 12, 2013

(30) Foreign Application Priority Data
Feb. 22, 2011 (EP) .................................. 11155281

(51) Int. Cl.
*A61B 6/00* (2006.01)
*G21K 1/00* (2006.01)
(Continued)

(52) U.S. Cl.
CPC . *G21K 1/00* (2013.01); *A61B 6/032* (2013.01); *A61B 6/4035* (2013.01); *A61B 6/4233* (2013.01); *A61B 6/482* (2013.01); *A61B 6/027* (2013.01); *A61B 6/4078* (2013.01)

(58) Field of Classification Search
CPC .......... G21K 1/00; A61B 6/027; A61B 6/032; A61B 6/4035; A61B 6/4078; A61B 6/4233; A61B 6/482

USPC ........................................................ 378/5, 19
See application file for complete search history.

(56) References Cited

U.S. PATENT DOCUMENTS 4,255,664 A  3/1981 Rutt et al.
5,570,403 A  10/1996 Yamazaki et al.
(Continued)

FOREIGN PATENT DOCUMENTS

EP  1384440 A2  1/2004
EP  1734405 A2  12/2006

OTHER PUBLICATIONS

Carmi, R., et al.; Material Separation with dual-layer CT; 2005; Nuclear Science Symposium Conference Record; IEEE; vol. 4; pp. 1876-1878.

(Continued)

*Primary Examiner* — Courtney Thomas (57) ABSTRACT

The invention relates to a detection apparatus comprising a filter (20) for filtering a conical radiation beam (4) such that at least a first region (22) and a second region (23) of the radiation beam are generated having different energy spectra, wherein the first region of the radiation beam illuminates a first detector area (25) on a detection surface (21) of a detector, thereby generating a first set of detection values, and the second region of the radiation beam illuminates a second detector area (26) on the detection surface, thereby generating a second set of detection values. For example, by using the filter the detection apparatus can be used as dual-energy computed tomography apparatus, wherein, for instance, a standard computed tomography apparatus can be transformed to a dual-energy computed tomography apparatus by adding the filter to the standard computed tomography apparatus, preferentially without modifying the radiation source and the detector.

17 Claims, 8 Drawing Sheets

(51) Int. Cl.
*A61B 6/03* (2006.01)
*A61B 6/02* (2006.01)

(56) References Cited

U.S. PATENT DOCUMENTS

| 7,050,529 | B2 | 5/2006 | Hoffman | |
|---|---|---|---|---|
| 2003/0147502 | A1 | 8/2003 | Heismann et al. | |
| 2004/0017879 | A1* | 1/2004 | Hoffman | 378/4 |
| 2007/0177713 | A1* | 8/2007 | Kohler et al. | 378/4 |
| 2009/0184251 | A1 | 7/2009 | Karim et al. | |
| 2010/0074393 | A1 | 3/2010 | Thran et al. | |
| 2010/0119035 | A1* | 5/2010 | Karch | 378/19 |
| 2010/0172464 | A1 | 7/2010 | Pavlovich et al. | |

OTHER PUBLICATIONS

Cho, P. S., et al.; Cone-beam CT for radiotherapy applications; 1995; Phys. Med. Biol.; 40:1863-1883.

Stolzmann, P., et al.; Dual Source CT: Detecting Urinary Stones by Spiral Dual Energy Computed Tomography with Virtual Non-Enhanced Images; 2007; SOMATOM Sessions; pp. 49-51.

* cited by examiner

DETECTION APPARATUS

FIELD OF THE INVENTION

The invention relates to a detection apparatus, a detection method and a detection computer program.

BACKGROUND OF THE INVENTION

The article "Dual Source CT: Detecting Urinary Stones by Spiral Dual Energy Computed Tomography With Virtual Non-Enhanced Images" by Paul Stolzmann et al., SOMATOM Sessions, pages 49 to 51, November 2007 discloses a dual-energy computed tomography apparatus comprising two x-ray tubes emitting x-rays with different energy spectra. The x-rays, after having traversed a region of interest, are detected by a detector, while the two x-rays tubes are rotated around the region of interest for illuminating the region of interest in different directions. The detector generates two sets of detection values, which correspond to the two x-ray spectra of the two x-ray tubes, and a reconstruction unit reconstructs two images of the region of interest from the two sets of detection values. This dual-energy computed tomography apparatus is technically relative complex.

SUMMARY OF THE INVENTION

It is an object of the invention to provide a detection apparatus, a detection method and a detection computer program, which allow generating different sets of detection values, which correspond to different energy spectra, with reduced technical complexity.

In a first aspect of the present invention a detection apparatus is presented, wherein the detection apparatus comprises:
- a radiation source for generating a conical radiation beam for traversing a region at interest within an examination zone,
- a detector with a homogenous detection surface for generating detection values being indicative of the radiation beam after having traversed the region of interest,
- a moving unit for moving the radiation source and the region of interest relative to each other along a helical trajectory around a rotational axis for allowing the radiation beam to traverse the region of interest in different directions, while the detector generates the detection values,
- a filter for filtering the radiation beam such that at least a first region and a second region of the radiation beam are generated having different energy spectra, wherein the first region of the radiation beam illuminates a first detector area on the detection surface, thereby generating a first set of detection values, and the second region of the radiation beam illuminates a second detector area on the detection surface, thereby generating a second set of detection values,
- a control unit for controlling the detection apparatus such that the first set of detection values and the second set of detection values are redundant.

By using the filter different sets of detection values, which correspond to different energy spectra, can be generated in a technically relatively simple way. For example, by using the filter the detection apparatus can be used as dual-energy computed tomography apparatus, wherein, for instance, a standard computed tomography apparatus can be transformed to a dual-energy computed tomography apparatus by adding the filter to the standard computed tomography apparatus, preferentially without modifying the radiation source and the detector.

The filter can create different energy filtrations for different detector pixels of the detector. The filter is adapted such that the first region of the radiation beam is differently filtered in comparison to the second region of the radiation beam. For example, a first half of the radiation beam can be differently filtered in comparison to a second half of the radiation beam. The filter can comprise different materials, different thicknesses, different densities, et cetera for filtering the first region and the second region of the radiation beam differently. The filter can be adapted to filter further regions of the radiation beam differently. For instance, a third, a fourth, et cetera region of the radiation beam can all be filtered differently.

The first region and the second region are located preferentially side-by-side, wherein the first region and the second region are neighbored in the direction of the rotational axis.

The border between the first detector area and the second detector area can enclose an angle with the rotational axis within a range of 0 and 90 degrees. In a preferred embodiment, this angle is 90 degrees. In a further preferred embodiment, this angle is larger than 0 degrees and smaller than 90 degrees.

In an embodiment, the filter is adapted such that the first region of the radiation beam is filtered and the second region of the radiation beam is unfiltered. This allows providing a first set of detection values and a second set of detection values, which correspond to different energy spectra, in a relatively simple way.

In a further embodiment, the detector, the radiation source and the filter are adapted such that the first detector area is a first half of the detection surface of the detector and the second detector area is a second half of the detection surface of the detector, wherein the first half of the detection surface and the second half of the detection surface are neighbored in the direction of the rotational axis. Also this allows generating two sets of detection values, which are redundant and which correspond to different energy spectra, in a relatively simple way.

The filter can be adapted such that at least one of the first region and the second region comprises geometrically disjunctive sub-regions having equal energy spectra, i.e. the sub-regions of a region have the same energy spectra.

In an embodiment, the filter is adapted such that the first region comprises two sub-regions enclosing the second region in the direction of the rotational axis. That means that a first sub-region of the first region, the second region and a second sub-region of the first region are neighbored side-by-side in this sequence in the direction of the rotational axis. It is preferred that the filter is adapted such that the detection apparatus is operable in an acquisition mode, in which the second region of the radiation beam illuminates the second detector area such that it includes at least a Tam-Danielsson window on the detection surface and the two sub-regions of the first region of the radiation beam illuminate two sub-detector areas of the first detector area. If the second detector area includes at least the Tam-Danielsson window on the detection surface, a corresponding second set of detection values can be generated, which is mathematically exact and, thus, allows a reconstruction with reduced artifacts. Since the Tam-Danielsson window is centered on the detection surface with respect to the rotational axis, the radiation beam has preferentially a central second region and two sub-regions of the first region at larger cone angles, wherein the two sub-regions of the first region have been filtered in the same way and comprise therefore the same energy spectra and wherein the second region is filtered differently and comprises another energy spectrum.

In an embodiment, the filter is adapted such that borders between the second detector area and the two sub-detector areas of the first detector area form straight lines. Since the borders form straight lines, the filter can relative easily be manufactured. Moreover, the straight lines lead to redundant data within the second detector area, which can be used for reducing noise in an image reconstructed from the second set of detection values. The filter can be adapted such that the borders between the second detector area and the two sub-detector areas of the first detector area enclose an angle of 90 degrees with the rotational axis. Such a filter is even easier to manufacture.

It is preferred that the filter is adapted such that the detection apparatus is operable in an acquisition mode in which the sets of detection values are complete data sets. In particular, two or more complete data sets can be provided by the sets of detection values, wherein each set of detection values is complete in the sense that an entire region of interest can be reconstructed exactly or approximately independently of the detection values of the other sets. In other words, the filter can be adapted to split the Radon space in several distinct portions, wherein the region of interest can be reconstructed from one of these portions of the Radon space independently from the other portions of the Radon space. The portions, i.e. the corresponding sets of detection values, are redundant and spectrally different.

Preferentially, a set of detection values is complete, if all object points to be reconstructed were irradiated over at least 180 degrees by the respective region of the radiation beam. The filter is preferentially adapted such that for a low pitch of the helical trajectory at least two sets of detection values can be generated, which fulfill the completeness criterion. In particular, the detection apparatus is preferably operable such that these distinct sets of detection values can simultaneously be generated, i.e. in a single scan.

In a preferred embodiment, the detection apparatus further comprises a reconstruction unit for reconstructing a first image of the region of interest from the first set of detection values and second image of the region of interest from the second set of detection values. It is preferred that the reconstruction unit is adapted to apply a component decomposition technique to the first and second images for determining a first component attenuation image, which is indicative of an attenuation caused by a first attenuation component within the region of interest, and a second component attenuation image, which is indicative of an attenuation caused by a second attenuation component within the region of interest. The reconstruction unit can be adapted to apply a decomposition technique which determines more than two component attenuation images. For example, three or more attenuation components can be considered. The attenuation components can represent materials like different base materials within the region of interest, for example, bone, soft tissue, contrast agent et cetera, and/or the attenuation components can represent different physical effects like the photoelectric effect and the Compton effect.

The detection apparatus can be adapted for at least one of the following applications: material separation, contrast agent mapping, virtual non-contrast imaging, mono-energetic imaging. For contrast agent mapping a contrast agent is preferentially located within the region of interest. The contrast agent can comprise iodine which is visible in computed tomography images.

Material separation can be performed by considering different materials within the region of interest as the different attenuation components. For example, first and second images can be determined, wherein the first image only shows a first material and the second image only shows a second material.

In computed tomography scans where contrast agent contrast is administered it can be important to obtain a map of the distribution of contrast agent in the human body, at least qualitatively. This can be achieved from the two spectral data sets by (a) identifying each image voxel using both reconstructed images as a voxel containing contrast agent or not and (b) quantifying the amount of contrast agent with the help of the respective absorption values in the first and second images, in particular, with the help of the respective Hounsfield unit values in the two images. The so-obtained images are regarded as being contrast agent maps. From the contrast agent maps and the two spectral data sets, it is also possible to derive virtual non-contrast images that display the anatomic image information and suppress the hyper-dense regions in the spectral images due to contrast agent, resembling a native CT scan. Finally, mono-energetic images can be displayed where the local voxel values are derived from the corresponding voxel values in the two spectral images and approximate the attenuation of the tissue at a given energy.

In an embodiment, at least one of the radiation source and the detector are adapted for generating energy-resolved detection data such that the different sets of detection values are divided into sub-sets of detection values which correspond to different energies. For example, the detector can be an energy-resolving detector for generating energy-resolved detection data such that the different sets of detection values are divided into sub-sets of detection values which correspond to different energies. The detector can comprise a dual-layer, in which two scintillator crystals are mounted on top of each other, a construction for resolving the detection values into two energies. In the dual-layer technique, low-energy photons are preferably registered in the front-layer and high-energy photons in the rear-layer leading to two spectrally distinct effective spectra for the detectors. In combination with a filter, which generates two sets of detection values, which correspond to two different energies, four sub-sets of detection values, which correspond to four different energies, can be generated. Thus, the detection apparatus can be adapted to perform quad-energy computed tomography. In addition or alternatively, the radiation source can be adapted to emit X-rays having different energy spectra. For example, the radiation source can comprise two X-ray tubes emitting X-rays with different energy spectra. During the acquisition of the detection values the two X-ray tubes can alternately emit X-rays for generating energy-resolved detection data. In combination with a filter, which generates two sets of detection values, which correspond to two different energies, four sub-sets of detection values, which correspond to four different energies, can be generated.

In a further aspect of the present invention a detection method is presented, wherein the detection method comprises:

generating a conical radiation beam for traversing a region of interest within an examination zone by a radiation source, generating detection values being indicative of the radiation beam after having traversed the region of interest by a detector with a homogenous detection surface, moving the radiation source and the region of interest relative to each other along a helical trajectory around a rotational axis for allowing the radiation beam to traverse the region of interest in different directions, while the detector generates the detection values, by a moving unit, filtering the radiation beam such that at least a first region and a second region of the radiation beam are generated having different energy spectra by a filter, wherein the first region of the radiation beam illuminates a first detector area on the detection surface, thereby generating a first set of detection values, and the second region of the radiation beam illuminates a second detector area on the detection surface, thereby generating a second set of detection values, controlling the detection apparatus such that the first set of detection values and the second set of detection values are redundant by a control unit.

In a further aspect of the present invention a detection computer program is presented, wherein the detection computer program comprises program code means for causing a detection apparatus as defined in claim 1 to carry out the steps of the detection method as defined in claim 14, when the detection computer program is run on a computer controlling the detection apparatus.

It shall be understood that the detection apparatus of claim 1, the detection method of claim 14, and the detection computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
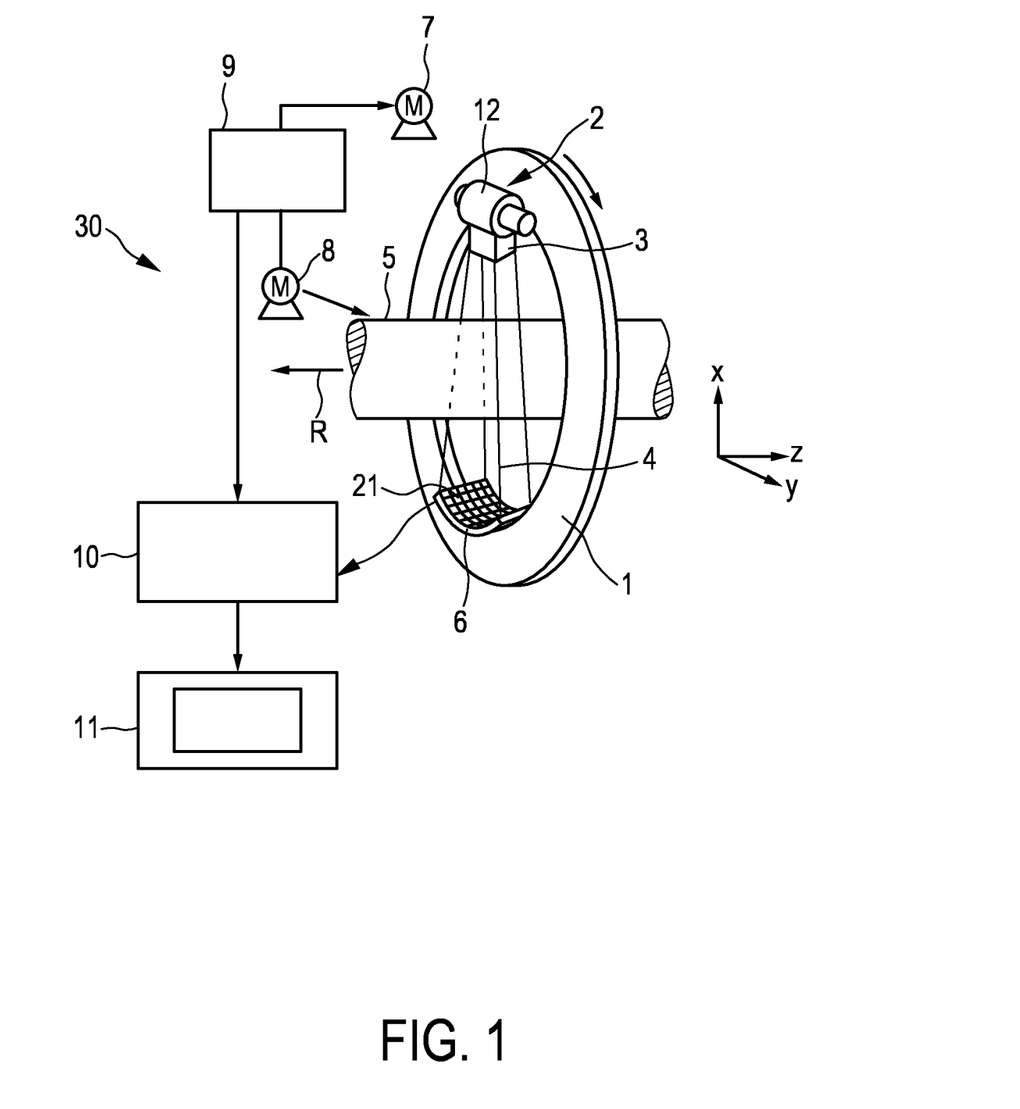
FIG. 1 shows schematically and exemplarily a representation of a detection apparatus being a computed tomography apparatus.

FIG. 1 shows schematically and exemplarily a detection apparatus being a computed tomography apparatus for imaging a region of interest within an examination zone 5. The computed tomography apparatus 30 includes a gantry 1 which is capable of rotation about a rotational axis R which extends parallel to the z direction. A radiation source 2 generates a conical radiation beam 4 for traversing the examination zone 5. The radiation source 2 comprises an X-ray tube 12 and a collimator 3 which forms the conical radiation beam 4 from the radiation generated by the X-ray tube 12. The radiation 4 traverses an object (not shown), such as a patient, and a region of interest, which is preferentially located within the object, in the region of interest, which is, in this embodiment, cylindrical. After having traversed the region of interest the radiation beam 4 is incident on a detector 6 comprising a two-dimensional homogenous detection surface 21, wherein different detector pixels of the detector are constructed similarly as usual in standard computed tomography apparatuses. The detector 6 is mounted on the gantry 1.

Figure 2:
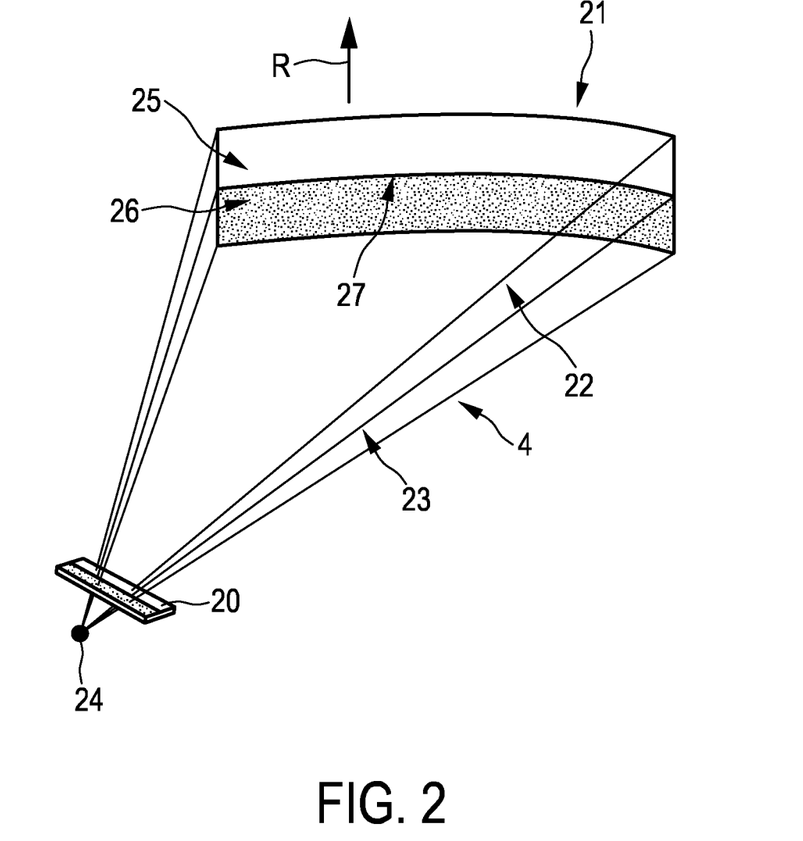
FIG. 2 shows schematically and exemplarily a representation of a filter for filtering a radiation beam of the detection apparatus.

The computed tomography apparatus 30 further comprises a filter 20, which is schematically and exemplarily shown in FIG. 2. FIG. 2 only shows some components of the computed tomography apparatus 30, which are needed for showing the function of the filter 20. The filter 20 can be integrated within the collimator 3, or the filter 20 can be arranged such that it filters the radiation before or after collimation.

The filter 20 filters the radiation beam 4, which emanates from a focal spot 24, such that a first region 22 and a second region 23 of the radiation beam 4 are generated having different energy spectra. The first region 22 of the radiation beam 4 generates a first set of detection values and the second region 23 of the radiation beam 4 generates a second set of detection values. The filter 20 is adapted such that the first region 22 of the radiation beam 4 is differently filtered in comparison to the second region 23 of the radiation beam 4. In particular, a first half of the radiation beam 4 is differently filtered in comparison to a second half of the radiation beam 4. The filter 20 can comprise different materials, different thicknesses, different densities, etc. for filtering the first region 22 and the second region 23 of the radiation beam 4 differently. In other embodiments, the filter can be adapted to filter further regions of the radiation beam 4 differently. For instance, a third, a fourth, etc. region of the radiation beam 4 can all be filtered differently. The first region 22 and the second region 23 are located side-by-side, wherein the first region 22 and the second region 23 are neighbored in the direction of the rotational axis R.

In this embodiment, the first region 22 of the radiation beam 4 illuminates a first detector area 25 on the detection surface 21, thereby generating the first set of detection values, and the second region 23 of the radiation beam 4 illuminates a second detector area 26 on the detection surface 21, thereby generating the second set of detection values In particular, the detector 6, the radiation source 2 and the filter 20 are adapted such that the first detector area 25 is a first half of the detection surface 21 of the detector 6 and the second detector area 26 is a second half of the detection surface 21 of the detector 6, wherein the first detector area 25 of the detection surface 21 and the second detector area 26 of the detection surface 21 are neighbored in the direction of the rotational axis R.

Figure 3:
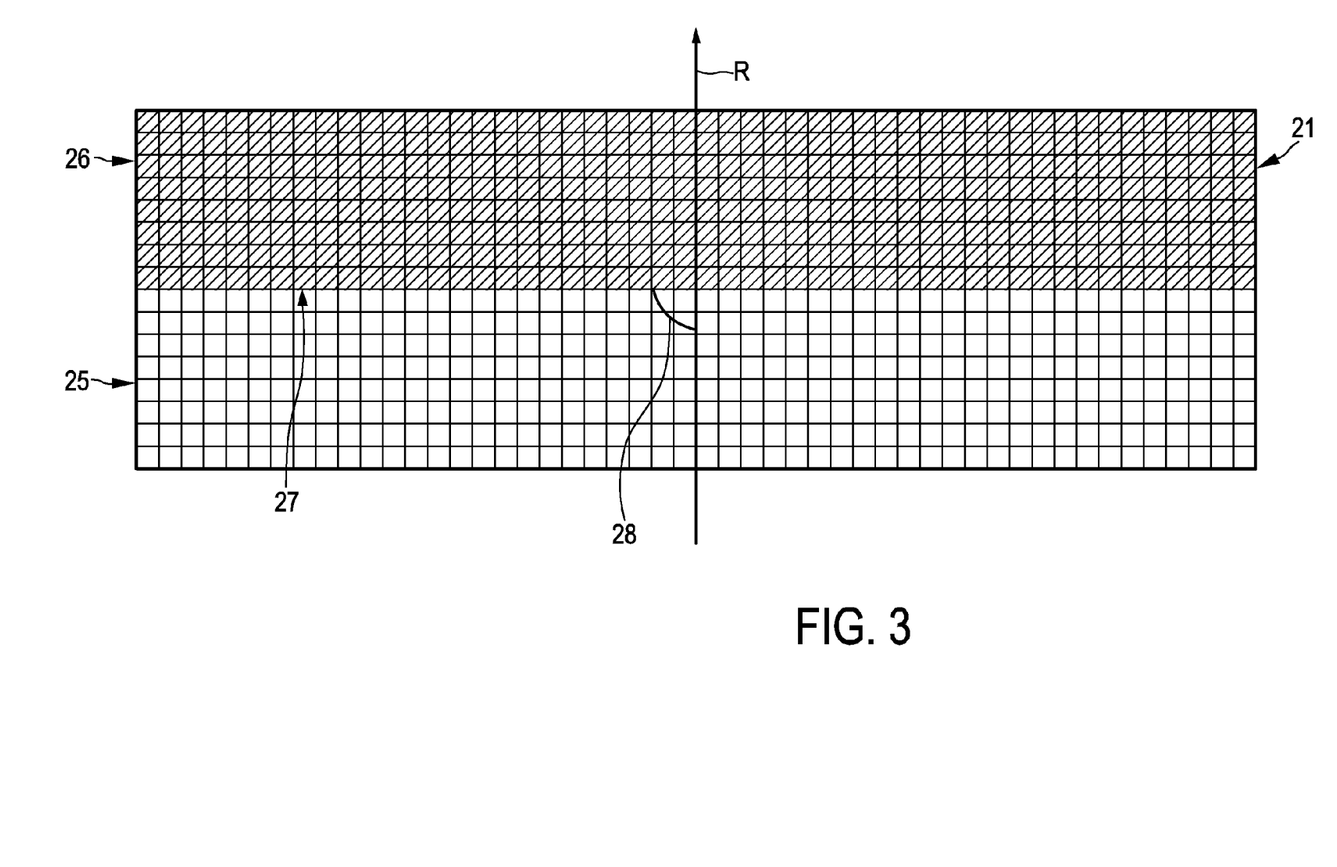
FIGS. 3 and 4 show exemplarily illuminations of a detection surface of a detector of the computed tomography apparatus.

The first detector area 25 and the second detector area 26 are also shown in FIG. 3. A border 27 between the first detector area 25 and the second detector area 26 encloses an angle 28 with the rotational axis R of 90 degrees. However, this angle can also have another value, which may be almost zero, and the border between different detector areas, which correspond to different regions of the radiation beam, do not need to be straight lines, but can also be curved lines.

Figure 4:
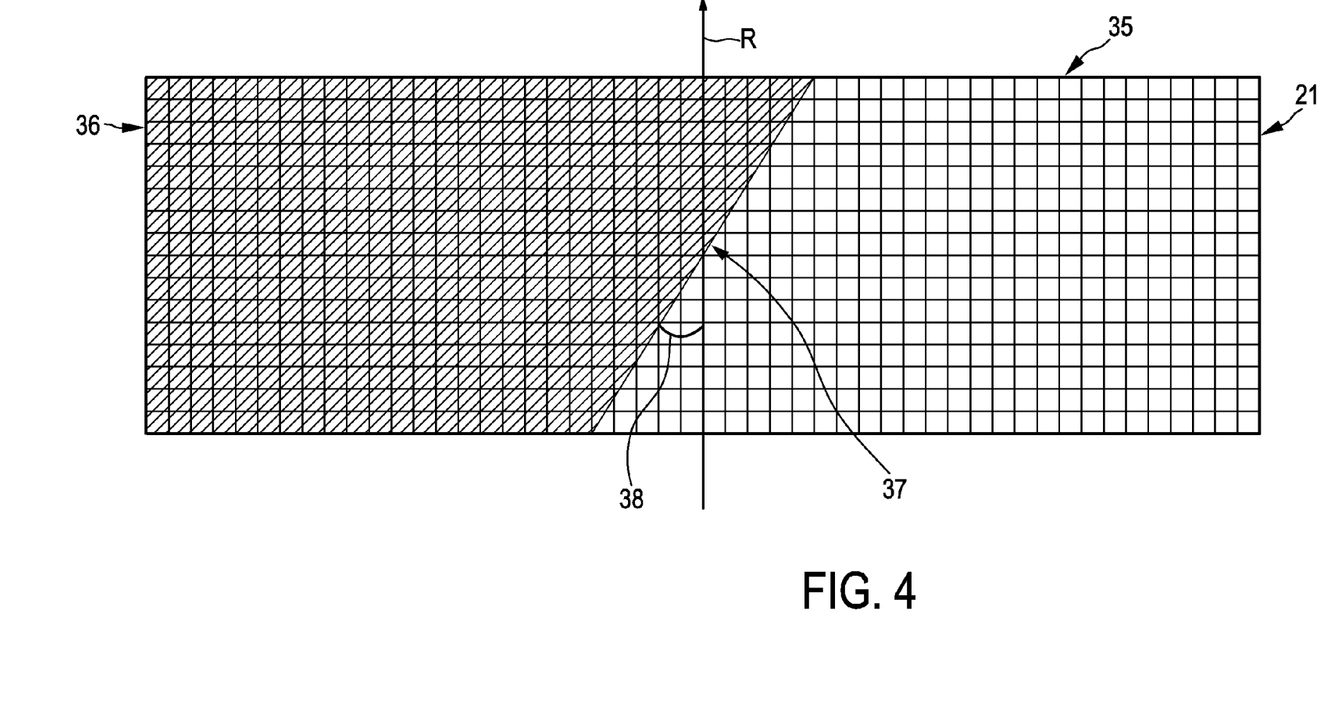

FIG. 4 shows schematically and exemplarily another illumination of the detection surface 21. In accordance with FIG. 4, the detector, the radiation source and the filter can be adapted such that a first detector area 35, which is illuminated by a first region of the filtered radiation beam, and a second detector area 36, which is illuminated by a second region of the filtered radiation beam, are separated by a border 37 which encloses an angle 38 being larger than 0 degrees and smaller than 90 degrees. In comparison to an angle of zero degrees, detection values, which correspond to the center of rotation can be used, since the border 37 is not aligned with the rotational axis R. Preferentially, the angle 38 is within a range of 10 to 30 degrees.

The computed tomography apparatus comprises two motors 7, 8. The gantry is driven at a preferably constant but adjustable angular speed by the motor 7. The motor 8 is provided for displacing the object, for example, a patient, who is arranged on a patient table in the examination zone 5, parallel to the direction of the rotational axis R or the z axis. The motors 7, 8 are controlled by a control unit 9 such that the radiation source 2 and the region of interest within the examination zone 5 move relative late to each other along a helical trajectory. The gantry 1 and the motor 7, 8 can be regarded as being a moving unit for moving the radiation source 2 and the region of interest relative to each other along the helical trajectory around the rotational axis R for allowing the radiation beam 4 to traverse the region of interest in different directions, while the detector 6 generates the detection values. During the relative movement of the radiation source 2 and the region of interest the detector 6 generates detection values being indicative of the radiation beam 4 after having traversed the region of interest.

The control unit 9 is adapted to control the computed tomography apparatus 30 such that the first set of detection values and the second set of detection values are redundant. In particular, the filter 20 is adapted such that the computed tomography apparatus is controllable in an acquisition mode in which the sets of detection values are complete data sets. Preferentially, two or more complete sets of detection values can be provided, wherein each set of detection values is complete in the sense that an entire region of interest can be reconstructed exactly or approximately independently of the detection values of the others. In other words, the filter 20 is preferentially adapted to split the Radon space in several distinct portions, wherein the region of interest can be reconstructed from one of these portions of the Radon space independently from the other portions of the Radon space. These portions, i.e. the corresponding sets of detection values, are redundant and spectrally different.

A set of detection values is complete, if all points within the region of interest to be reconstructed are irradiated over at least 180° by the respective region of the radiation beam 4. The filter 20 is preferentially adapted such that for a low pitch of the helical trajectory at least two sets of detection values can be generated, which each fulfill the completeness criterion. In particular, the computed tomography apparatus 30 is operable such that these distinct sets of detection values can be generated simultaneously, i.e. in a single scan.

The different sets of detection values, which are, in this embodiment, different sets of projection data, are provided to a reconstruction unit 10 for reconstructing a first image of the region of interest from the first set of detection values and a second image of the region of interest from the second set of detection values. The control unit 9 controls preferentially also the reconstruction unit 10. The reconstruction unit 10 can be adapted to use a reconstruction algorithm like a filtered backprojection algorithm, an algebraic reconstruction algorithm, a Radon inversion algorithm, et cetera for reconstructing the first image from the first set of detection values and the second image from the second set of detection values.

The reconstruction unit 10 is further adapted to apply a component decomposition technique to the first and second images for determining a first component attenuation image, which is indicative of an attenuation caused by a first attenuation component within the region of interest, and a second component attenuation image, which is indicative of an attenuation caused by a second attenuation component within the region of interest. For example, the different attenuation components within the region of interest can be different materials like bone, soft tissue, a contrast agent, et cetera, and/or the attenuation components within the region of interest can relate to different physical effects like a Compton effect, a photo-electric effect, a K-edge effect, et cetera.

The component decomposition technique can be performed in accordance with following equations:

$$\mu(E_1,x,y)=\mu_1^B(E_1)\rho_1(x,y)+\mu_2^B(E_1)\rho_2(x,y) \text{ and} \quad (1)$$

$$\mu(E_2,x,y)=\mu_1^B(E_2)\rho_1(x,y)+\mu_2^B(E_2)\rho_2(x,y). \quad (2)$$

In equations (1) and (2) $\mu(E_1,x,y)$ denotes the first image, $\mu(E_2,x,y)$ denotes the second image, $E_1$ denotes the mean energy of the first region of the filtered radiation beam, $E_2$ denotes the mean energy of the second region of the filtered radiation beam, x,y denote spatial coordinates within the respective image, $\mu_1^B(E)$ denotes the known energy-dependent attenuation function for the first attenuation component, $\mu_2^B(E)$ denotes the known energy-dependent attenuation function for the second attenuation component, $\rho_1(x,y)$ denotes an unknown density of the first attenuation component and $\rho_2(x,y)$ denotes an unknown density of the second attenuation component. By using the two equations (1) and (2) the two unknown densities $\rho_1(x,y)$ and $\rho_2(x,y)$ can be determined. In equations (1) and (2) only two spatial coordinates x and y are used, i.e. equations (1) and (2) refer to two-dimensional images. However, equations (1) and (2) can similarly be used for three-dimensional images.

The reconstruction unit 10 is preferentially adapted for at least one of the following applications: material separation, contrast agent mapping, virtual non-contrast imaging and mono-energetic imaging.

Material separation is performed by considering different materials like bone, soft tissue, a contrast agent, et cetera within the region of interest as the different attenuation components. For example, first and second component attenuation images can be determined, wherein the first component attenuation image only shows a first material and the second component attenuation image only shows a second material. For instance, a bone image, a soft tissue image and/or a contrast agent image can be determined as the component attenuation images.

For contrast agent mapping, the reconstruction unit 10 is preferentially adapted to generate a contrast agent map, in particular, an iodine map, if the contrast agent present within the region of interest is iodine. The contrast agent map describes the distribution of the contrast agent within the region of interest, for example, within a human body present in the region of interest, at least qualitatively. The reconstruction unit can be adapted to generate the contrast agent map from the first image and the second image by (a) identifying each image voxel using both reconstructed images as a voxel containing the contrast agent or not and (b) quantifying the amount of contrast agent by using the absorption values, in particular, the Hounsfield unit values, in the first and second images. The identification of each image element using both reconstructed images as an image element containing the contrast agent or not can be performed, for example, by studying the location of the image elements in a two-dimensional scatter plot, wherein the two axes of the two-dimensional scatter plot are defined by $\mu(E_1, x,y)$ and $\mu(E_2, x,y)$. A predefined separation line can be provided in the two-dimensional scatter plot, wherein image elements, which are separated from the other image elements which may represent, for example, calcifications by the separation line, contain the contrast agent. The separation line can be predefined by, for example, calibration measurements. This identification of an image voxel as a voxel containing the contrast agent or not and a possible quantification of the amount of contrast agent is disclosed in more detail in "Material Separation with Dual-Layer CT" by R. Carmi et al., Proceedings of IEEE Nuclear Symposium 2005, Conference record 2005; 4: 1876-1878, 2005, which is herewith incorporated by reference.

A virtual non-contrast image shows, for example, anatomic image information, wherein hyper-dense regions, which are hyper-dense because of contrast agent, are suppressed, thereby generating a native computed tomography scan. The reconstruction unit 10 can be adapted to generate a virtual non-contrast image from the generated contrast agent map and the first and second images. For example, from the contrast agent map, in particular, from the iodine map, the contribution of the contrast agent to the total attenuation can be estimated for each image element, in particular, for each voxel, labeled as containing the contrast agent. For estimating the contribution of the contrast agent to the total attenuation of the respective image element, the approximate amount of the contrast agent in the respective image element as defined by the contrast agent map and the known attenuation curve for the contrast agent can be used. By subtracting this estimate from the first and second images, virtual non-contrast images can be reconstructed, independently for each of the first and second images.

A mono-energetic image comprises image values, in particular, voxel values, which are derived from the corresponding image values in the first image and the second image, wherein the image values of the mono-energetic image approximate the attenuation within the region of interest at a given energy.

Mono-energetic images can be derived from equations (1) and (2) above once the density images $\rho_1(x,y)$ and $\rho_2(x,y)$ are determined. In particular, since the density images have been determined and the energy-dependent attenuation functions $\mu_1^B(E)$ and $\mu_2^B(E)$ are known, a mono-energetic image $\mu(E, x,y)$ can be determined for an arbitrary energy E in accordance with following equation:

$$\mu(E,x,y)=\mu_1^B(E)\rho_1(x,y)+\mu_2^B(E)\rho_2(x,y). \quad (3)$$

This can be done for arbitrary energies so that an entire energy-dependent attenuation curve can be displayed for every voxel independently.

The generated images can be provided to a display 11 for displaying the images.

Figure 5:
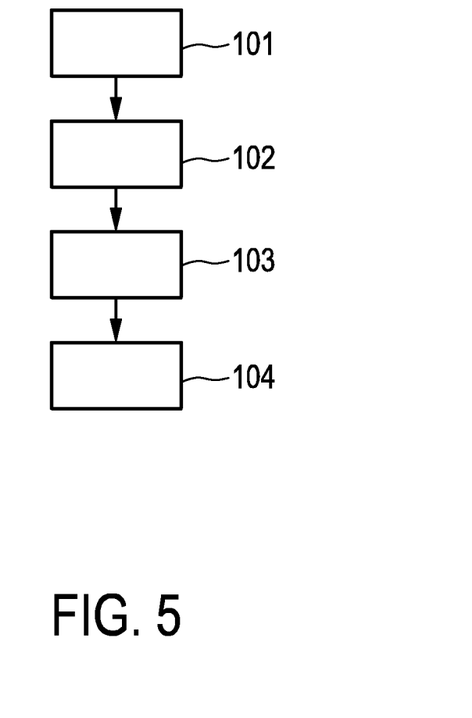
FIG. 5 shows exemplarily a flowchart illustrating an embodiment of a detection method being a computed tomography method.

In the following an embodiment of a detection method will exemplarily be described with reference to a flowchart shown in FIG. 5.

In step 101, a conical radiation beam is generated by the radiation source 2 for traversing the region of interest in the examination zone 5. The detector 6 generates detection values being indicative of the radiation 4 after having traversed the region of interest while the moving unit 1, 7, 8 moves the radiation source 2 and the region of interest relative to each other along a helical trajectory around a rotational axis for allowing the radiation beam 4 to traverse the region of interest in different directions. The detection values are generated by the detector 6 having the homogeneous detection surface 21. Before traversing the region of interest, the radiation beam 4 is filtered by the filter 20 in a direction of the rotational axis R such that at least a first region 22 and a second region 23 of the radiation beam 4 are generated having different energy spectra, wherein the first region 22 of the radiation beam 4 generates a first set of detection values and the second region 23 of the radiation beam 4 generates a second set of detection values. During the generation of the detection values, the control unit 9 controls the computed tomography apparatus such that the first set of detection values and the second set of detection values are redundant.

In step 102, the reconstruction unit 10 reconstructs a first image of the region of interest from the first set of detection values and a second image of the region of interest from the second set of detection values. In step 103, the reconstruction unit 10 applies a component decomposition technique to the first and second images for determining a first component attenuation image, which is indicative of an attenuation caused by a first attenuation component within the region of interest, and a second component attenuation image, which is indicative of an attenuation caused by a second attenuation component within the region of interest. In step 104, the display 11 shows at least one of the first component attenuation image and the second component attenuation image. The reconstruction unit 10 can also generate further images like a contrast agent map, a virtual non-contrast image or a mono-energetic image, which can be shown on the display 11, as an alternative or in addition to the first attenuation component image and the second attenuation component image.

The above described computed tomography apparatus can be realized by, for example, modifying state-of-the-art products for computed tomography. Functionality for dual-energy applications can be offered without sophisticated hardware changes. In particular, two or more different spectral measurements can be realized, without modifying either the X-ray tube or the X-ray detector of a non-energy-resolving computed tomography apparatus by using, for example, the filter 20. A filter, which may also be regarded as being an aperture filter mask, can be brought in an X-ray cone beam to create different filtrations for different detector pixels, wherein the detection values are detected in a helical computed tomography acquisition mode.

For low pitch helical computed tomography acquisition modes the data in Radon space are characterized by a rather high degree of redundancy. Generally, in approximate reconstruction methods for these acquisition modes appropriate weighting schemes have to be used to treat those redundancies and reconstruct images within a reconstruction field of view, i.e. of a region of interest. The computed tomography apparatus described above with reference to FIG. 1 resolves these redundancies by using the filter 20, which is a quasi-binary filter mask that splits data in the Radon space into two distinct portions. Preferentially, each of the portions is complete in the sense that it is possible to approximately reconstruct the entire region of interest independently of the data of the other portion in Radon space. In an embodiment, the filter is designed in such a way that the two portions of Radon data can be geometrically redundant, but spectrally as distinct as possible. In an embodiment, this can be achieved by masking one half of the detection surface with an X-ray filter to be brought close to the focal spot of the X-ray tube, while keeping the other half of the beam unfiltered, or filtered differently or weaker.

For reconstructing the first and second images the reconstruction unit 10 can be adapted to perform an aperture-weighted wedge reconstruction algorithm for reconstruction the first and second images.

Although in the embodiment described above with reference to FIGS. 1 and 2, the filter 20 has a certain structure, in other embodiments the filter can have another structure. The filter is preferentially adapted to optimize a separation of data in the Radon space for the reconstruction of two or more volume data sets. In an embodiment, the filter can be adapted such that at least one of the first region and the second region of the radiation beam comprises geometrically disjunctive sub-regions having equal energy spectra, i.e. the sub-regions of a region have the same energy spectra. This filter is preferentially adapted such that the first region comprises two sub-regions enclosing the second region in the direction of the rotational axis R. That means that a first sub-region of the first region, the second region and a second sub-region of the first region are neighbored side-by-side in this sequence in the direction of the rotational axis R. The filter can be adapted such that the computed tomography apparatus is operable in an acquisition mode, in which the second region of the radiation beam illuminates at least a Tam-Danielsson window on the detection surface and the two sub-regions of the first region of the radiation beam illuminate the remaining parts of the detection surface. The filter can therefore be adapted such that the illumination of the Tam-Danielsson window can be guaranteed. This can allow for the reconstruction of the first and second images unaffected by penumbra effects, which may be generated by boundaries of a binary filter, like the filter 20 shown in FIG. 2, on the detector.

Figure 6:
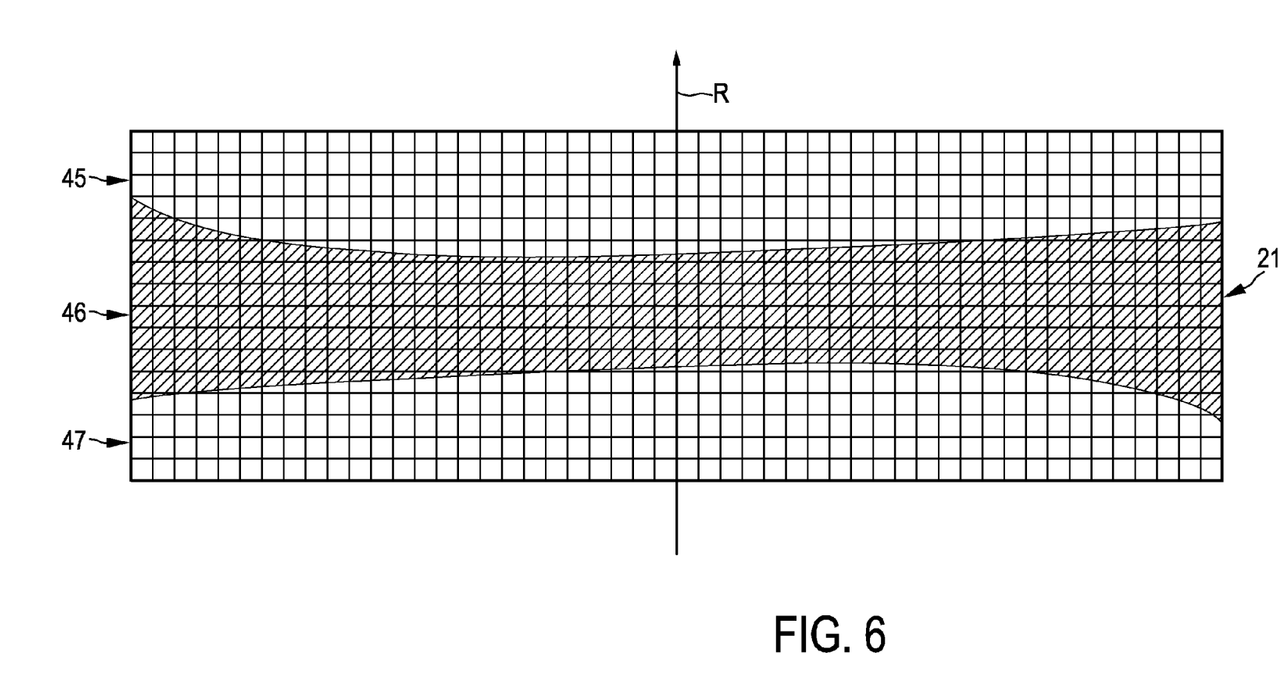
FIGS. 6 to 8 show exemplarily further illuminations of the detection surface, wherein a central detector area and outer detector areas are illuminated differently and wherein the inner central detector area includes a Tam-Danielsson window.

FIG. 6 shows schematically and exemplarily the detection surface 21, wherein two sub-detector areas 45, 47 of a first detector area are illuminated by a first region of the filtered radiation beam and wherein a second detector area 46 of the detection surface 21 is illuminated by a second region of the filtered radiation beam. In FIG. 6, the second detector area 46 is the Tam-Danielsson window.

Figure 7:
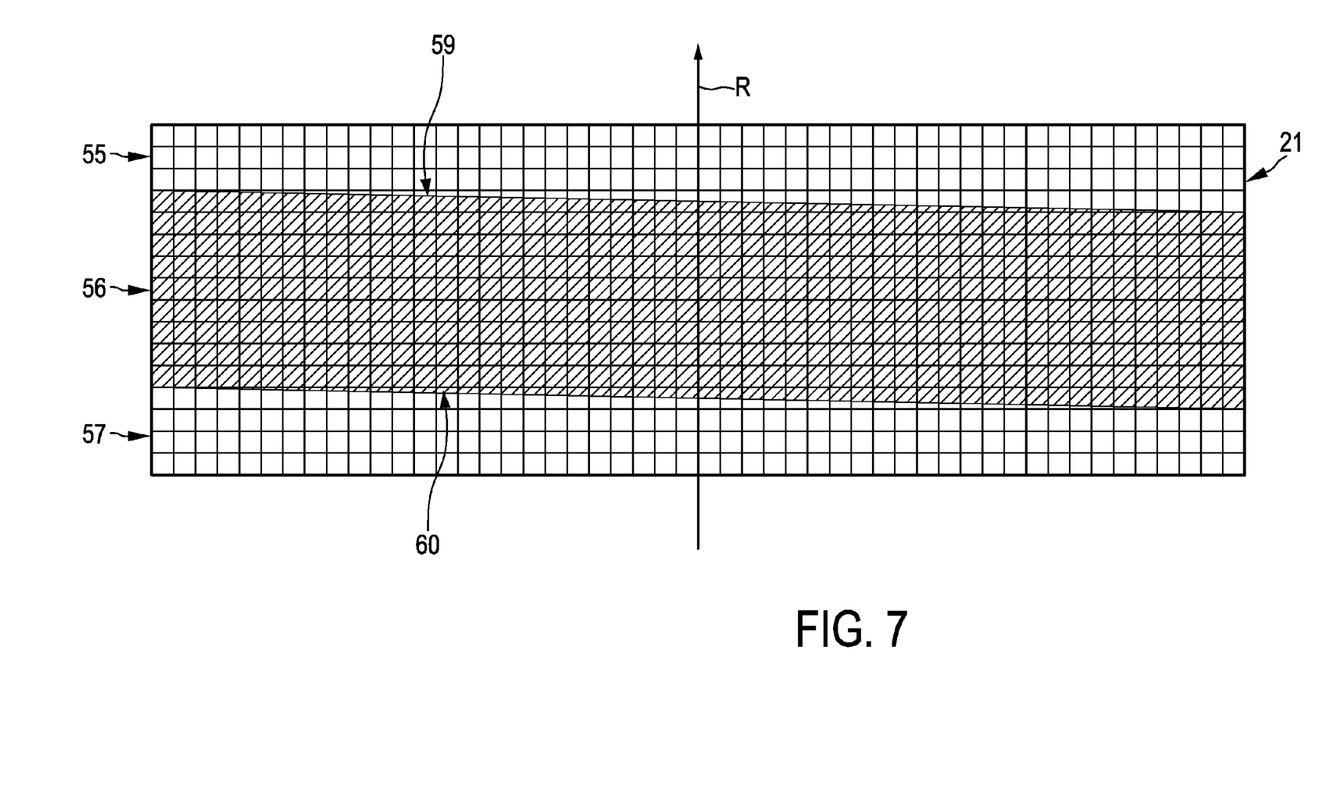

FIG. 7 shows schematically and exemplarily a further possible illumination of the detection surface 21. In this embodiment, the filter is adapted such that the detection apparatus is operable in an acquisition mode, in which the second region of the radiation beam illuminates a second detector area 56, which includes and is larger than the Tam-Danielsson window on the detection surface 21, and two sub-regions of a first region of the radiation beam illuminate two sub-detector areas 55, 57 forming a second detector area on the detection surface 21. In FIG. 7, the borders 59, 60 between the first detector area 55, 57 and the second detector area 56 are straight lines, which are not perpendicular to the rotational axis R.

Figure 8:
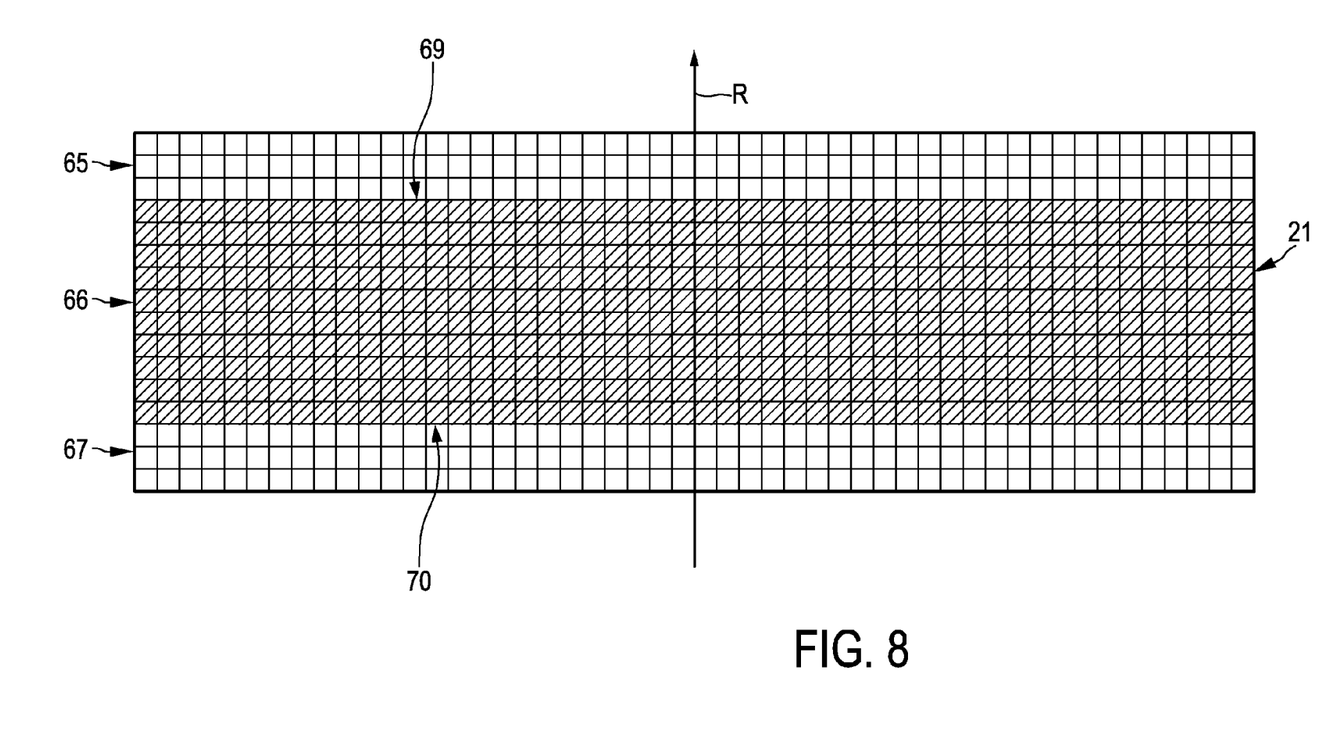

FIG. 8 shows schematically and exemplarily a further possible illumination of the detection surface 21. Also in this embodiment the filter is adapted such that the detection apparatus is operable in an acquisition mode, in which the second region of the radiation beam illuminates a second detector area 66 such that it includes and is larger than the Tam-Danielsson window on the detection surface 21 and sub-regions of a first region of the filtered radiation beam illuminate two sub-detector areas 65, 67 of the first detector area. In this embodiment, the borders 69, 70 are straight lines and perpendicular to the rotational axis R.

The reconstruction unit can be adapted to apply an aperture weighted wedge reconstruction algorithm to the first set of detection values for reconstructing a first image and to the second set of detection values for reconstructing a second image. If the borders between the first and second detector areas are not straight lines perpendicular to the rotational axis, the filtering of the detection values performed during the aperture weighted wedge reconstruction can be adapted such that the transverse truncation of the detection values is considered. This adaptation can be performed by using a data extension like Cho-matching, where complementary detection values, i.e. detection values from an opposite source position, are used to create untruncated detection values. The data extension is disclosed, for example, in the article "Cone-beam CT for radiotherapy applications" by Paul S. Cho et al., Phys. Med. Biol. 40 (1995) 1863 to 1883, which is herewith incorporated by reference. A rebinning into wedge geometry can be performed either before or after the data extension. After a ramp filtering, the detection values can be back-projected. The detection values, which correspond to the second detector area shown in FIGS. 7 and 8 correspond to a region on the detection surface 21, which is larger than the Tam-Danielsson window. Redundant detection values are therefore provided in the second detector area that allow for overscan weighting.

The reconstruction unit can also be adapted to perform any other reconstruction algorithm. For example, the reconstruction unit can be adapted to perform an iterative reconstruction as described, for example, in the article "Statistical image reconstruction methods for transmission tomography" by Fessler in Handbook of Medical Imaging, Vol. 2, SPIE Press, edited by J. M. Fritzpatrick and M. Sonka, pages 1-70 (2000), which is herewith incorporated by reference.

Although in the embodiment described above with reference to FIGS. 1 and 2 the detector is a non-energy-resolving detector, the detector can also be an energy-resolving detector for generating energy-resolved detection values such that the different sets of detection values are divided into sub-sets of detection values which correspond to different energies. For example, the detector can comprise a dual-layer, in which two scintillator crystals are mounted on top of each other, a construction for resolving the detection values into two energies. Low-energy photons are preferably registered in the front layer and high energy photons are preferentially registered in the rear layer leading to two spectrally distinct effective spectra. In combination with a filter, which generates two sets of detection values, which correspond to two different energies, four sub-sets of detection values, which correspond to four different energies, can be generated. Thus, the computed tomography apparatus can be adapted to perform quad-energy computed tomography. The four sub-sets of detection values can be used for reconstructing four images, wherein for each of the four sub-sets of detection values a single image is reconstructed. These four images can be used for improving the accuracy of quantifying, for example, a contrast material within a region of interest.

Although in the above described embodiments the detection apparatus is a computed tomography apparatus, which also comprises a reconstruction unit for reconstructing images from the different sets of detection values, the detection apparatus can also not comprise a reconstruction unit and, thus, just provide the different sets of detection values, wherein the reconstruction can be performed by another apparatus.

Although in the above described embodiments the contrast agent maps, the virtual non-contrast image and the mono-energetic image are generated in a certain way, in other embodiments the contrast agent map, the virtual non-contrast image and the mono-energetic image can also be determined in another way. The first image, the second image, the contrast agent map, the virtual non-contrast image, the mono-energetic image, et cetera can be two-dimensional or three-dimensional.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations like the reconstruction of the first and second images or the decomposition technique performed by one or several units or devices can be performed by any other number of units or devices. For example, steps 102 and 103 can be performed by a single unit or by any other number of different units. The calculations and/or the control of the detection apparatus in accordance with the detection method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a detection apparatus comprising a filter for filtering a conical radiation beam such that at least a first region and a second region of the radiation beam are generated having different energy spectra, wherein the first region of the radiation beam illuminates a first detector area on a detection surface of a detector, thereby generating a first set of detection values, and the second region of the radiation beam illuminates a second detector area on the detection surface, thereby generating a second set of detection values. For example, by using the filter the detection apparatus can be used as dual-energy computed tomography apparatus, wherein, for instance, a standard computed tomography apparatus can be transformed to a dual-energy computed tomography apparatus by adding the filter to the standard computed tomography apparatus, preferentially without modifying the radiation source and the detector.

The invention claimed is:

1. A detection apparatus, the detection apparatus comprising:
    a radiation source configured to generate a conical radiation beam for traversing a region of interest within an examination zone;
    a detector with a homogenous detection surface configured to generate detection values being indicative of the radiation beam after having traversed the region of interest;
    a moving unit configured to move the radiation source and the region of interest relative to each other along a helical trajectory around a rotational axis (R) for allowing the radiation beam to traverse the region of interest in different directions, while the detector generates the detection values;
    a filter configured to filter and divide the radiation beam into a first contiguous region and a second contiguous region and the first contiguous region having different energy spectra from the second contiguous region, wherein the first contiguous region of the radiation beam illuminates a first detector area on the detection surface, thereby generating a first set of detection values, and the second contiguous region of the radiation beam illuminates a second detector area on the detection surface, thereby generating a second set of detection values, and the filter is non-moving relative to the radiation source;
    a control unit configured to control the detection apparatus such that the first set of detection values and the second set of detection values are redundant; and
    wherein the filter is adapted such that the detection apparatus is operable in an acquisition mode in which the sets of detection values are complete data sets that include the region of interest.

2. The detection apparatus as defined in claim 1, wherein the filter is adapted such that the first contiguous region of the radiation beam is filtered and the second contiguous region of the radiation beam is unfiltered.

3. The detection apparatus as defined in claim 1, wherein the detector, the radiation source and the filter are adapted such that the first detector area is a first half of the detection surface of the detector and the second detector area is a second half of the detection surface of the detector, wherein the first detector area of the detection surface and the second detector area of the detection surface are neighbored in the direction of the rotational axis (R).

4. The detection apparatus as defined in claim 1, wherein a border between the first detector area and the second detector area encloses an angle with the rotational axis (R) less than 90 degrees.

5. The detection apparatus as defined in claim 1, wherein the detection apparatus further comprises a reconstruction unit for reconstructing a first image of the region of interest from the first set of detection values and a second image of the region of interest from the second set of detection values.

6. The detection apparatus as defined in claim 5, wherein the reconstruction unit is adapted to apply a component decomposition technique to the first and second images for determining a first component attenuation image, which is indicative of an attenuation caused by a first attenuation component within the region of interest, and a second component attenuation image, which is indicative of an attenuation caused by a second attenuation component within the region of interest.

7. The detection apparatus as defined in claim 5, wherein the reconstruction unit is adapted for at least one of the following applications: material separation, contrast agent mapping, virtual non-contrast imaging, mono-energetic imaging.

8. The detection apparatus as defined in claim 1, wherein at least one of the radiation source and the detector are adapted for generating energy-resolved detection data such that the different sets of detection values are divided into sub-sets of detection values which correspond to different energies.

9. A non-transitory storage medium comprising-program code controlling the control unit as defined in claim 1.

10. The detection apparatus as defined in claim 1, wherein the filter is adapted such that the first region and the second region include all of the generated conical radiation beam detected by the homogenous detection surface.

11. The detection apparatus as defined in claim 1, wherein the filter is adapted such that the first region comprises one contiguous region adjacent the second region comprising one contiguous region.

12. The detection apparatus as defined in claim 10, wherein the filter is adapted such that the first region and the second region are the same size.

13. A detection method, the detection method comprising:
    generating a conical radiation beam for traversing a region of interest within an examination zone by a radiation source;
    generating detection values being indicative of the radiation beam after having traversed the region of interest by a detector with a homogenous detection surface;
    moving the radiation source and the region of interest relative to each other along a helical trajectory around a rotational axis (R) for allowing the radiation beam to traverse the region of interest in different directions, while the detector generates the detection values, by a moving unit;

filtering the radiation beam by a filter dividing the filtered radiation beam into a first contiguous region and a second contiguous region having different energy spectra, wherein the first contiguous region of the radiation beam illuminates a first detector area on the detection surface, thereby generating a first set of detection values, and the second contiguous region of the radiation beam illuminates a second detector area on the detection surface, thereby generating a second set of detection values, and the filter is non-moving relative to the radiation source;

controlling the detection apparatus such that the first set of detection values and the second set of detection values are redundant of a region of interest by a control unit and are complete data sets.

14. The method as defined in claim 13, wherein filtering of the second region by the filter illuminates the second detector surface such that it includes at least a Tam-Danielsson window.

15. The method as defined in claim 13, wherein a border between the first detector area and the second detector area encloses an angle with the rotational axis (R) less than 90 degrees.

16. A detection apparatus, the detection apparatus comprising:

a radiation source configured to generate a conical radiation beam for traversing a region of interest within an examination zone;

a detector with a homogenous detection surface configured to generate detection values being indicative of the radiation beam after having traversed the region of interest;

a moving unit configured to move the radiation source and the region of interest relative to each other along a helical trajectory around a rotational axis (R) for allowing the radiation beam to traverse the region of interest in different directions, while the detector generates the detection values;

a filter configured to filter the radiation beam divided into a first region and a second region of the radiation beam and filtered having different energy spectra, wherein the first region of the radiation beam illuminates a first detector area on the detection surface, thereby generating a first set of detection values, and the second region of the radiation beam illuminates a second detector area on the detection surface, thereby generating a second set of detection values, and the second region is a contiguous region;

a control unit configured to control the detection apparatus such that the first set of detection values and the second set of detection values are redundant of the region of interest; and wherein the filter is adapted such that the detection apparatus is operable in an acquisition mode, in which the second region of the radiation beam illuminates the second detector area such that it includes at least a Tam-Danielsson window on the detection surface and two sub-regions of the first region of the radiation beam illuminate two sub-detector areas of the first detector area.

17. The detection apparatus as defined in claim 16, wherein the filter is adapted such that borders between the second detector area and the two sub-detector areas of the first detector area form straight lines.

* * * * *